(12) United States Patent
Hu et al.

(10) Patent No.: US 11,987,673 B2
(45) Date of Patent: May 21, 2024

(54) METHOD TO CONVERT WASTE PLASTICS INTO VALUE-ADDED CHEMICALS USING MICROWAVE-ASSISTED CATALYSIS

(71) Applicant: West Virginia University Board of Governors on Behalf of West Virginia University, Morgantown, WV (US)

(72) Inventors: Jianli Hu, Morgantown, WV (US); Yuxin Wang, Morgantown, WV (US)

(73) Assignee: West Virginia University Board of Governors on Behalf of West Virginia University, Morgantown, WV (US)

( * ) Notice: Subject to any disclaimer, the term of this patent is extended or adjusted under 35 U.S.C. 154(b) by 0 days.

(21) Appl. No.: 17/307,683

(22) Filed: May 4, 2021

(65) Prior Publication Data

US 2021/0347960 A1    Nov. 11, 2021

Related U.S. Application Data

(60) Provisional application No. 63/021,318, filed on May 7, 2020.

(51) Int. Cl.
| | | |
|---|---|---|
| C08J 11/16 | (2006.01) | |
| B01J 19/12 | (2006.01) | |
| B01J 19/24 | (2006.01) | |
| B01J 19/30 | (2006.01) | |
| B01J 29/40 | (2006.01) | |
| B01J 35/61 | (2024.01) | |
| C07C 4/22 | (2006.01) | |

(52) U.S. Cl.
CPC ............. *C08J 11/16* (2013.01); *B01J 19/12* (2013.01); *B01J 19/2415* (2013.01); *B01J 19/30* (2013.01); *B01J 29/40* (2013.01); *B01J 35/615* (2024.01); *C07C 4/22* (2013.01); *B01J 2219/0801* (2013.01); *B01J 2219/0871* (2013.01); *B01J 2219/0892* (2013.01); *B01J 2219/3086* (2013.01); *C07C 2521/12* (2013.01); *C07C 2529/40* (2013.01); *C08J 2323/06* (2013.01)

(58) Field of Classification Search
CPC ........ C08J 11/16; C08J 2323/06; B01J 19/12; B01J 19/2415; B01J 19/30; B01J 29/40; B01J 35/1019; B01J 2219/0801; B01J 2219/0871; B01J 2219/0892; B01J 2219/3086; B01J 8/02; B01J 2219/1206; B01J 19/126; C07C 4/22; C07C 2521/12; C07C 2529/40; Y02P 20/52; Y02W 30/62
See application file for complete search history.

(56) References Cited

U.S. PATENT DOCUMENTS 6,184,427 B1 * 2/2001 Klepfer ................... C10G 1/10
                                                        201/2.5

* cited by examiner

*Primary Examiner* — Thuan D Dang
(74) *Attorney, Agent, or Firm* — Thomas | Horstemeyer, LLP

(57) ABSTRACT

In one aspect, the disclosure relates to a method for converting waste plastics into value-added products, the method including the steps of (a) contacting the waste plastics with a catalyst to form a reaction mixture and (b) applying microwave irradiation to the reaction mixture. In another aspect, disclosed herein are value-added products including, but not limited to, aromatic and aliphatic hydrocarbons produced by the process disclosed herein. This abstract is intended as a scanning tool for purposes of searching in the particular art and is not intended to be limiting of the present disclosure.

14 Claims, 5 Drawing Sheets

FIG. 2A  FIG. 2B

METHOD TO CONVERT WASTE PLASTICS INTO VALUE-ADDED CHEMICALS USING MICROWAVE-ASSISTED CATALYSIS

CROSS-REFERENCE TO RELATED APPLICATIONS

This Application claims the benefit of U.S. Provisional Application No. 63/021,318, filed on May 7, 2020, which is incorporated herein by reference in its entirety.

BACKGROUND

Nearly 40 million tons of plastic waste were generated in the United States in 2019, with more than 80% of being sent to landfills. In order to reduce plastic disposal in landfills, numerous methods have been developed to recover the energy from the plastic wastes as value added products such as BTX chemicals (i.e., benzene, toluene, and xylenes), ethylene, and/or hydrogen. For example, thermal decomposition of long chain plastic into shorter chain hydrocarbons to produce liquid fuel and chemicals has been widely studied over last two decades. Processes explored include pyrolysis, gasification, cracking, and pyrolysis coupled with reforming. Catalysts have been explored as a method for improving system efficiency and optimizing product distribution. Most plastic thermal decomposition processes operate over 500° C., with the products mainly consisting of waxes with boiling points in the 500-650° C. range. With heating from 650-800° C., aromatics are produced with around 20% yield. Over 800° C., light olefins are produced with yields up to 70%. In order to produce more of the higher value products at moderate reaction condition, integrated fluid catalytic cracking (FCC) units for cracking of plastic-derived waxes at around 500° C. have been constructed. Although known thermal decomposition process may produce liquid fuels and valued chemicals from waste plastics, their high costs and complexity have thus far prohibited widespread use of thermal decomposition of plastic wastes.

Ethylene has a high market potential as a basic platform chemical for the synthesis of numerous other industrially-important chemicals. The global ethylene market size was valued at $92 billion in 2018. The expanded need for plastics, fibers, and organic chemicals, among other products, drives the demand of this market. Further, the global ethylene market is estimated to grow at a compound annual growth rate (CAGR) of 6.2% from 2019 to 2026, reaching $137 billion by 2026.

Meanwhile, the global BTX aromatic market size was valued at $163 billion in 2018. BTX are primarily used in the manufacturing of chemicals, intermediates and consumer products such as paints, thinner, rubber product, adhesives, ink, cosmetics, pharmaceutical products, among others. BTX are naturally present in gasoline and are also used as gasoline additives as well as additives in various simulation fluids to improve the flow of hydrocarbons during production. The global BTX market is projected to grow significantly at a CAGR of 5.9% from 2019 to reach $275 billion by 2027.

Despite advances in plastic waste conversion research, there is still a scarcity of methods that offers high yields of value-added chemicals in a single step while using less energy and requiring less capital investment than currently available processes. Such methods would further reduce plastic landfill waste and strengthen energy security by providing a domestic source of BTX aromatics, ethylene, and other value-added chemicals. These needs and other needs are satisfied by the present disclosure.

SUMMARY

In accordance with the purpose(s) of the present disclosure, as embodied and broadly described herein, the disclosure, in one aspect, relates to a method for converting waste plastics into value-added products, the method including the steps of (a) contacting the waste plastics with a catalyst to form a reaction mixture and (b) applying microwave irradiation to the reaction mixture. In another aspect, disclosed herein are value-added products including, but not limited to, aromatic and aliphatic hydrocarbons produced by the process disclosed herein.

Disclosed herein are methods for converting a waste plastic to a value-added product, the method comprising: (a) contacting the waste plastic with a catalyst to form a reaction mixture; and (b) applying microwave radiation to the reaction mixture; thereby forming a value-added product.

Also disclosed are methods for converting a waste plastic to a value-added product, the method comprising: (a) providing waste plastic to a reactor; (b) contacting the waste plastic with a catalyst to form a reaction mixture; and (c) applying microwave radiation to the reaction mixture; thereby forming a value-added product; wherein the catalyst comprises a zeolite, a solid acid catalyst, or a combination thereof; wherein the waste plastic comprises low-density polyethylene, high-density polyethylene, polypropylene, polystyrene, polyethylene terephthalate, polyurethane, clothing fibers, an epoxy plastic, or a combination thereof; and wherein the value-added product comprises benzene, toluene, xylenes, ethylene, hydrogen, methane, or a combination thereof.

Also disclosed are compositions comprising at least one value-added product produced using a disclosed method.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 2A-2C show a schematic of microwave-assisted and thermal catalytic decomposition mechanisms and representative data comparing of gas production for microwave heating at two temperatures versus thermal heating. FIG. 2A shows a mechanism schematic for microwave-assisted catalytic decomposition of waste plastic. FIG. 2B shows a mechanism schematic for conventional thermal decomposition of waste plastic. In the mechanism schematic representations shown in FIGS. 2A-2B, relatively colder spots are indicated by lighter gray circles and relatively hotter spots are indicated by dark gray circles. FIG. 2C shows data of gas production as a result of using a disclosed microwave-assisted catalytic decomposition method carried out at two different bulk temperatures as indicated in the figure versus conventional thermal degradation of waste plastic carried out at the indicated temperature.

FIG. 3A shows a schematic of microwave-assisted catalyic decomposition of plastic waste. In the figure, the catalysts are shown as being relatively hotter (dark gray spots) or colder (light gray spots), and the interaction of reactant materials with the relatively different catalyst temperatures results in catalyzed reactions that provide light olefins (relatively hotter catalysts) or hydrogen gas via aromatization (relatively colder catalysts). FIG. 3B shows gas composition and carbon selectivity for various heating times using a disclosed microwave-assisted catalytic decomposition method.

Figure 1:
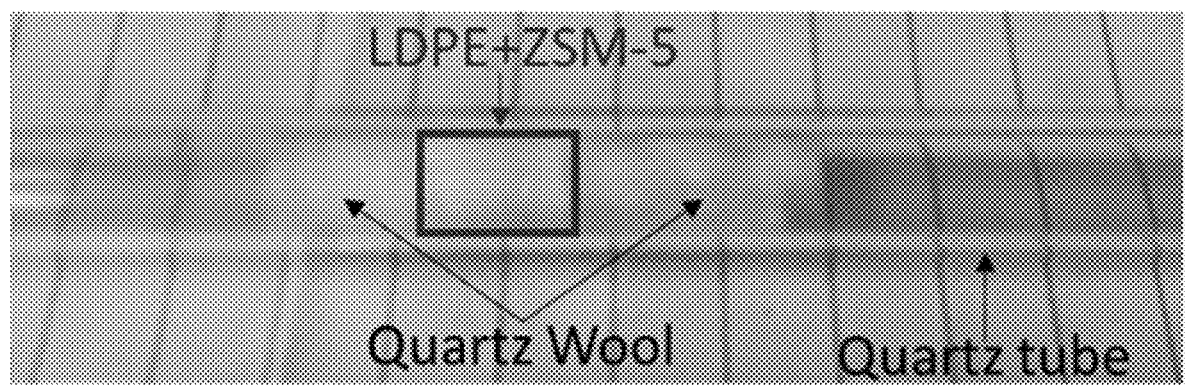
FIG. 1 shows a reaction chamber useful herein. For some experiments, catalyst (ZSM-5) and waste plastic were ground to micron size particles and placed between segments of loose quartz wool packing material in a quartz reaction tube.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a catalyst," "a promoter metal," or "a value-added product," includes, but is not limited to, mixtures of two or more such catalysts, promoter metals, or value-added products, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a catalyst refers to an amount that is sufficient to achieve the desired improvement in the property modulated by the formulation component, e.g. achieving the desired level of waste plastic conversion and/or the desired product specificity. The specific level in terms of wt % in a composition required as an effective amount will depend upon a variety of factors including the amount and type of waste plastic, microwave power and resultant reaction temperature, particle size of both the catalyst and the waste plastic, and the desired product profile.

As used herein, the terms "optional" or "optionally" means that the subsequently described event or circumstance can or cannot occur, and that the description includes instances where said event or circumstance occurs and instances where it does not.

As used herein, "BTX" refers to a mixture containing one or more of a benzene, a toluene, and a xylene. The relative amounts of each present in the mixture is not constrained by the term BTX, and all such mixtures are contemplated by the present disclosure.

"Waste plastic" as used herein is any plastic material (e.g., low-density polyethylene, high-density polyethylene, polypropylene, polystyrene, polyethylene terephthalate, polyurethane, clothing fibers, epoxy plastics, and the like) that would otherwise be discarded. In some aspects, waste plastic is post-consumer waste (e.g., food containers, personal care product containers, and the like). In other aspects, waste plastic can be discarded after use in a healthcare or industrial setting, or can be a byproduct of an industrial process, or the like.

"Value-added products" as used herein refers to decomposition products of waste plastic decomposition that have further industrial uses such as, for example, as fuels or fuel additives, solvents, or intermediates for synthesis of other products. Value-added products produced by the processes disclosed herein include, but are not limited to, benzene, toluene, xylenes, methane, ethylene, hydrogen, and other aliphatic and aromatic hydrocarbons.

A "zeolite" as used herein refers to an aluminosilicate mineral with a microporous structure. Zeolites are, in one aspect, useful as catalysts for the processes disclosed herein. Zeolites can occur naturally or can be produced industrially.

A "solid acid" catalyst is an acidic catalyst that does not dissolve in the reaction medium. Solid acid catalysts can be Lewis acids, metal oxides, or the like, and, in one aspect, are useful as catalysts for the processes disclosed herein.

A "promoter" as used herein refers to a substance added to a catalyst to improve catalytic performance. In one aspect, a promoter can interact with a catalyst and alter its effect on the reaction in question, although promoters may not have catalytic effects on their own. In one aspect, promoters can be metal ions or atoms incorporated into metal oxides. Promoters useful herein include, but are not limited to Pt, Pd, Ru, Rh, Co, Mb, Ni, Fe, Mn, and combinations thereof.

"Microwave irradiation" refers to electromagnetic irradiation with a frequency of from about 0.3 to about 300 GHz. In one aspect, in the method disclosed herein microwave irradiation can be applied to a mixture of a catalyst and waste plastic in order to convert the waste plastic into one or more value-added products.

Unless otherwise specified, temperatures referred to herein are based on atmospheric pressure (i.e. one atmosphere).

Catalytic Conversion of Waste Plastics to Value-Added Products

In one aspect, disclosed herein is a method for converting a waste plastic to a value-added product, the method comprising: (a) contacting the waste plastic with a catalyst to form a reaction mixture; and (b) applying microwave radiation to the reaction mixture; thereby forming a value-added product.

Also disclosed are methods for converting a waste plastic to a value-added product, the method comprising: (a) providing waste plastic to a reactor; (b) contacting the waste plastic with a catalyst to form a reaction mixture; and (c) applying microwave radiation to the reaction mixture; thereby forming a value-added product; wherein the catalyst comprises a zeolite, a solid acid catalyst, or a combination thereof; wherein the waste plastic comprises low-density polyethylene, high-density polyethylene, polypropylene, polystyrene, polyethylene terephthalate, polyurethane, clothing fibers, an epoxy plastic, or a combination thereof; and wherein the value-added product comprises benzene, toluene, xylenes, ethylene, hydrogen, methane, or a combination thereof.

Waste Plastics

Disclosed herein is a method for converting a waste plastic into one or more value-added product including, but not limited to, benzene, toluene, xylenes, ethylene, hydrogen, methane, or combinations thereof. In one aspect, the waste plastic can be a polyolefin. In a further aspect, the polyolefin can be a low-density polyethylene (LDPE), high-density polyethylene (HDPE), polypropylene (PP), polystyrene (PS), polyethylene terephthalate (PET), polyurethanes (PU), clothing fibers, an epoxy plastic, another plastic, or a combination thereof. In a further aspect, the waste plastic can be pelletized, chopped, cut, powdered, or otherwise reduced in size from bulk materials as presented in consumer and industrial plastic waste streams. In a yet further aspect, the waste plastic can be ground down to micron-sized particles prior to performing the method disclosed herein.

Catalysts

In one aspect, the methods disclosed utilize one or more catalyst. In one aspect, the catalyst can be selected from ZSM-5, a Y-zeolite, a zeolite supported catalyst, a fluid catalytic cracking catalyst, an aromatization catalyst, a solid acid catalyst, a USY zeolite, zeolite X, a rare-earth metal oxide supported catalysts, and combinations thereof.

In one aspect, when the catalyst is a zeolite, it can have a $SiO_2:Al_2O_3$ mole ratio of from about 20:1 to about 300:1, or of about 20:1, 25:1, 30:1, 35:1, 40:1, 45:1, 50:1, 55:1, 60:1, 65:1, 70:1, 75:1, 80:1, 90:1, 100:1, 150:1, 200:1, 250:1, 280:1, 300:1, or a combination of any of the foregoing values, or a range encompassing any of the foregoing values. In one aspect, the $SiO_2:Al_2O_3$ mole ratio is about 23:1.

In another aspect, when the catalyst is a zeolite, it can have a surface area of from about 400 to about 450 $m^2/g$, or of about 400, 405, 410, 415, 420, 425, 430, 435, 440, 445, or about 450 $m^2/g$, or a combination of any of the foregoing values, or a range encompassing any of the foregoing values. In one aspect, the surface area is about 425 $m^2/g$.

In a further aspect, the solid acid catalyst can be selected from $ZrO_2/SO_4$, $TiO_2/SO_4$, $HfO_2/SO_4$, $ZrO_2/WO_3$, $TiO_2/WO_3$, $HfO_2/WO_3$, or a combination thereof.

Catalyst Promoters

In some aspects, the catalysts disclosed herein can be used in combination with metal promoters including, but not limited to, platinum, palladium, ruthenium, rhenium, cobalt, molybdenum, nickel, iron, manganese, another metal, or a combination thereof. In one aspect, $Pt/ZrO_2/SO_4$ is a particularly effective catalyst.

Microwave Irradiation

In one aspect, the reactions disclosed herein can be conducted in a microwave reactor. In a further aspect, the microwave reactor can be a variable frequency reactor. In a further aspect, the frequency can be set from about 915 MHz to about 20 GHz, about 915 MHz to about 10 GHz, about 915 MHz to about 6.65 GHz, about 915 MHz to about 5 GHz, or at about 915, 950, or 975 MHz, or about 1, 1.5, 2, 2.5, 3, 3.5, 4, 4.5, 5, 5.5, 6, 6.5, or about 6.65 GHz, or a combination of any of the foregoing values, or a range encompassing any of the foregoing values. In any of these aspects, the microwave reaction temperature can be measured by a known method such as, for example, IR thermography.

Reaction Process

Sample Preparation and Reactor

In one aspect, the catalyst and waste plastic are ground up into small particles prior to performing the reactions disclosed herein. In a further aspect, the particles are approximately micron sized. In still another aspect, the catalyst:waste plastic mass ratio can be from about 0.1 to 20, or from about 1 to 10, or from about 1 to 5, or can be 0.1:20, 1:20, 1:15, 1:10, 1:9, 1:8, 1:7, 1:6, or about 1:5, or a combination of any of the foregoing values, or a range encompassing any of the foregoing values.

In another aspect, a mixed catalyst/plastic mass of about 0.5 g can be used in the reactions disclosed herein. In a further aspect, this mixture occupies a volume of about 0.6 cm³. However, in another aspect, the reaction can be scaled to another mass and volume to fit in a larger or differently-shaped reactor.

In one aspect, the reaction chamber can be a quartz tube. In another aspect, the reactor is a fixed-bed reactor. In a further aspect, the catalyst/plastic sample can be packed between two plugs of loose quartz wool.

In some aspects, the output gas composition can be measured by an inline gas chromatograph. In one aspect, a carrier gas can be used. In a further aspect, the carrier gas is an inert gas such as, for example, nitrogen. In still another aspect, the carrier gas can be introduced at room temperature and a flow rate of about 20 mL/min. Further in this aspect, the flow rate can be scaled depending on the size of the reactor. In another aspect, the carrier gas flow rate can be varied during the reaction.

Reaction Temperatures

In one aspect, the reaction temperature as measured by IR thermography can be from about 180° C. to about 400° C., or from about 250 to about 360° C., or can be about 180, 190, 200, 210, 220, 230, 240, 250, 260, 270, 280, 290, 300, 310, 320, 330, 340, 350, 360, 370, 380, 390, or about 400° C., or a combination of any of the foregoing values, or a range encompassing any of the foregoing values. In one aspect, the reaction temperature is about 260° C. In another aspect, the reaction temperature is about 360° C. In another aspect, the disclosed microwave-assisted reaction requires lower temperatures than traditional thermal heating but produces a greater yield of products.

Without wishing to be bound by theory, the catalyst particles absorb microwave radiation in the disclosed process and transfer heat to the waste plastic particles via conduction, as plastic waste typically has a low dielectric loss factor and cannot absorb microwave energy directly. Further in this aspect, both hot spots and cold spots exist within the reaction chamber. In one aspect, over the hot spots, plastic catalytically gasifies to form light olefins, while over the cold spots, the light olefins can aromatize and produce $H_2$ according to the following scheme:

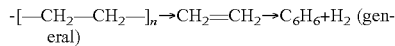
$-[-CH_2-CH_2-]_n \rightarrow CH_2=CH_2 \rightarrow C_6H_6 + H_2$ (general)

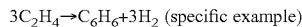
$3C_2H_4 \rightarrow C_6H_6 + 3H_2$ (specific example)

Reaction Times

In one aspect, the reaction can be carried out for any length of time required to obtain the desired product mixture. In a further aspect, the reaction can be carried out (i.e., microwave radiation can be applied) for from about 5 to about 30 minutes, or for about 5, 6, 7, 8, 9, 10, 11, 12, 13, 14, 15, 16, 17, 18, 19, 20, 21, 22, 23, 24, 25, 26, 27, 28, 29, or about 30 minutes, or a combination of any of the foregoing values, or a range encompassing any of the foregoing values.

Reaction Pressure

In one aspect, the reaction can be carried out at a pressure of from about 1 to about 20 atm, or from about 1 to about 10 atm, or at about 1, 2, 3, 4, 5, 6, 7, 8, 9, 10, 11, 12, 13, 14, 15, 16, 17, 18, 19, or about 20 atm, or a combination of any of the foregoing values, or a range encompassing any of the foregoing values.

Aspects

The following listing of exemplary aspects supports and is supported by the disclosure provided herein.

Aspect 1. A method for converting a waste plastic to a value-added product, the method comprising: (a) providing a waste plastic to a reactor; (b) contacting the waste plastic with a catalyst to form a reaction mixture; and (c) applying microwave radiation to the reaction mixture; thereby forming a value-added product; wherein the catalyst comprises a zeolite, a solid acid catalyst, rare-earth metal oxide catalyst, or a combination thereof; and wherein the value-added product comprises benzene, toluene, xylenes, ethylene, propylene, butene, hydrogen, methane, or a combination thereof.

Aspect 2. The method of Aspect 1, wherein the waste plastic comprises a material selected from a polyamide, a polycarbonate, a polyvinyl chloride, a polyester, a polyolefin, an epoxy, and combinations thereof.

Aspect 3. The method of Aspect 2, wherein the waste plastic comprises a polyolefin.

Aspect 4. The method of Aspect 3, wherein the polyolefin is selected from a polyolefin low-density polyethylene, a high-density polyethylene, a polypropylene, a polystyrene, and combinations thereof.

Aspect 5. The method of Aspect 1, wherein the waste plastic comprises a material selected from a low-density polyethylene, a high-density polyethylene, a polypropylene, a polystyrene, a polyethylene terephthalate, a polyurethane, an epoxy plastic, or a combination thereof.

Aspect 6. The method of Aspect 1, wherein the waste plastic comprises a textile, a fabric, a yarn, a clothing fiber, or combinations thereof.

Aspect 7. The method of Aspect 6, wherein the waste plastic is one or more fabric.

Aspect 8. The method of Aspect 7, wherein the one or more fabric comprises a woven fabric, a knit fabric, a non-woven fabric, or combinations thereof.

Aspect 9. The method of Aspect 1, wherein the waste plastic comprises low-density polyethylene.

Aspect 10. The method of any one of Aspect 1-Aspect 9, wherein the catalyst comprises a catalyst metal.

Aspect 11. The method of Aspect 10, wherein the catalyst metal comprises at least one metal selected from Groups 6-12.

Aspect 12. The method of Aspect 11, wherein the catalyst metal is selected from Ru, Pt, Pd, Cr, Mn, Fe, Co, Ni, Zn, and combinations thereof.

Aspect 13. The method of claim Aspect 11, wherein the catalyst metal is selected from Ru, Pd, Cr, Fe, Co, Ni, Zn, and combinations thereof.

Aspect 14. The method of claim Aspect 11, wherein the catalyst metal is selected from Ru, Pd, Fe, and combinations thereof.

Aspect 15. The method of Aspect 11, wherein the catalyst metal comprises a single metal selected from Groups 6-12.

Aspect 16. The method of claim Aspect 15, wherein the catalyst metal is selected from Ru, Pt, Pd, Cr, Mn, Fe, Co, Ni, Zn, and combinations thereof.

Aspect 17. The method of claim Aspect 16, wherein the catalyst metal is selected from Ru, Pd, Cr, Fe, Co, Ni, Zn, and combinations thereof.

Aspect 18. The method of claim Aspect 17, wherein the catalyst metal is selected from Ru, Pd, Fe, and combinations thereof.

Aspect 19. The method of claim Aspect 18, wherein the catalyst metal is Ru.

Aspect 20. The method of Aspect 11, wherein the catalyst metal comprises two metals selected from Groups 6-12.

Aspect 21. The method of claim Aspect 20, wherein the catalyst metal comprises two metals selected from Ru, Pt, Pd, Cr, Mn, Fe, Co, Ni, Zn, and combinations thereof.

Aspect 22. The method of claim Aspect 21, wherein the catalyst metal comprises two metals selected from Ru, Pd, Cr, Fe, Co, Ni, Zn, and combinations thereof.

Aspect 23. The method of claim Aspect 22, wherein the catalyst metal comprises two metals selected from Ru, Pd, Fe, and combinations thereof.

Aspect 24. The method of claim Aspect 20, wherein the catalyst metal comprises Ru and Fe.

Aspect 25. The method of claim Aspect 20, wherein the catalyst metal comprises Ru and Pd.

Aspect 26. The method of any one of Aspect 10-Aspect 25, wherein the catalyst metal is present in an amount from about 0.5 wt % to about 12 wt %.

Aspect 27. The method of claim Aspect 26, wherein the catalyst metal is present in an amount from about 0.5 wt % to about 10 wt %.

Aspect 28. The method of claim Aspect 26, wherein the catalyst metal is present in an amount from about 0.5 wt % to about 8 wt %.

Aspect 29. The method of claim Aspect 26, wherein the catalyst metal is present in an amount from about 0.5 wt % to about 6 wt %.

Aspect 30. The method of claim Aspect 26, wherein the catalyst metal is present in an amount from about 1 wt % to about 12 wt %.

Aspect 31. The method of claim Aspect 26, wherein the catalyst metal is present in an amount from about 1 wt % to about 10 wt %.

Aspect 32. The method of claim Aspect 26, wherein the catalyst metal is present in an amount from about 1 wt % to about 8 wt %.

Aspect 33. The method of claim Aspect 26, wherein the catalyst metal is present in an amount from about 1 wt % to about 6 wt %.

Aspect 34. The method of claim Aspect 26, wherein the catalyst metal is present in an amount from about 2 wt % to about 12 wt %.

Aspect 35. The method of claim Aspect 26, wherein the catalyst metal is present in an amount from about 2 wt % to about 10 wt %.

Aspect 36. The method of claim Aspect 26, wherein the catalyst metal is present in an amount from about 2 wt % to about 8 wt %.

Aspect 37. The method of claim Aspect 26, wherein the catalyst metal is present in an amount from about 2 wt % to about 6 wt %.

Aspect 38. The method of claim Aspect 26, wherein the catalyst metal is present in an amount from about 4 wt % to about 12 wt %.

Aspect 39. The method of claim Aspect 26, wherein the catalyst metal is present in an amount from about 4 wt % to about 10 wt %.

Aspect 40. The method of claim Aspect 26, wherein the catalyst metal is present in an amount from about 4 wt % to about 8 wt %.

Aspect 41. The method of claim Aspect 26, wherein the catalyst metal is present in an amount from about 4 wt % to about 6 wt %.

Aspect 42. The method of any one of Aspect 1-Aspect 9, wherein the rare-earth metal oxide catalyst comprises a catalyst metal and a catalyst support: wherein the catalyst metal comprises at least one metal selected from Groups 6-12; and wherein the catalyst support is selected from comprises $CeO_2$, $La_2O_3$, and combinations thereof.

Aspect 43. The method of Aspect 42, wherein the catalyst metal is selected from Ru, Pt, Pd, Cr, Mn, Fe, Co, Ni, Zn, and combinations thereof.

Aspect 44. The method of claim Aspect 43, wherein the catalyst metal is selected from Ru, Pd, Cr, Fe, Co, Ni, Zn, and combinations thereof.

Aspect 45. The method of claim Aspect 44, wherein the catalyst metal is selected from Ru, Pd, Fe, and combinations thereof.

Aspect 46. The method of Aspect 42, wherein the catalyst metal comprises a single metal selected from Groups 6-12.

Aspect 47. The method of claim Aspect 46, wherein the catalyst metal is selected from Ru, Pt, Pd, Cr, Mn, Fe, Co, Ni, Zn, and combinations thereof.

Aspect 48. The method of claim Aspect 47, wherein the catalyst metal is selected from Ru, Pd, Cr, Fe, Co, Ni, Zn, and combinations thereof.

Aspect 49. The method of claim Aspect 48, wherein the catalyst metal is selected from Ru, Pd, Fe, and combinations thereof.

Aspect 50. The method of claim Aspect 49, wherein the catalyst metal is Ru.

Aspect 51. The method of Aspect 42, wherein the catalyst metal comprises two metals selected from Groups 6-12.

Aspect 52. The method of claim Aspect 46, wherein the catalyst metal comprises two metals selected from Ru, Pt, Pd, Cr, Mn, Fe, Co, Ni, Zn, and combinations thereof.

Aspect 53. The method of claim Aspect 47, wherein the catalyst metal comprises two metals selected from Ru, Pd, Cr, Fe, Co, Ni, Zn, and combinations thereof.

Aspect 54. The method of claim Aspect 48, wherein the catalyst metal comprises two metals selected from Ru, Pd, Fe, and combinations thereof.

Aspect 55. The method of claim Aspect 54, wherein the catalyst metal comprises Ru and Fe.

Aspect 56. The method of claim Aspect 54, wherein the catalyst metal comprises Ru and Pd.

Aspect 57. The method of any one of Aspect 1-Aspect 56, wherein the catalyst metal is present in an amount from about 0.5 wt % to about 12 wt %.

Aspect 58. The method of claim Aspect 57, wherein the catalyst metal is present in an amount from about 0.5 wt % to about 10 wt %.

Aspect 59. The method of claim Aspect 57, wherein the catalyst metal is present in an amount from about 0.5 wt % to about 8 wt %.

Aspect 60. The method of claim Aspect 57, wherein the catalyst metal is present in an amount from about 0.5 wt % to about 6 wt %.

Aspect 61. The method of claim Aspect 57, wherein the catalyst metal is present in an amount from about 1 wt % to about 12 wt %.

Aspect 62. The method of claim Aspect 57, wherein the catalyst metal is present in an amount from about 1 wt % to about 10 wt %.

Aspect 63. The method of claim Aspect 57, wherein the catalyst metal is present in an amount from about 1 wt % to about 8 wt %.

Aspect 64. The method of claim Aspect 57, wherein the catalyst metal is present in an amount from about 1 wt % to about 6 wt %.

Aspect 65. The method of claim Aspect 57, wherein the catalyst metal is present in an amount from about 2 wt % to about 12 wt %.

Aspect 66. The method of claim Aspect 57, wherein the catalyst metal is present in an amount from about 2 wt % to about 10 wt %.

Aspect 67. The method of claim Aspect 57, wherein the catalyst metal is present in an amount from about 2 wt % to about 8 wt %.

Aspect 68. The method of claim Aspect 57, wherein the catalyst metal is present in an amount from about 2 wt % to about 6 wt %.

Aspect 69. The method of claim Aspect 57, wherein the catalyst metal is present in an amount from about 4 wt % to about 12 wt %.

Aspect 70. The method of claim Aspect 57, wherein the catalyst metal is present in an amount from about 4 wt % to about 10 wt %.

Aspect 71. The method of claim Aspect 57, wherein the catalyst metal is present in an amount from about 4 wt % to about 8 wt %.

Aspect 72. The method of claim Aspect 57, wherein the catalyst metal is present in an amount from about 4 wt % to about 6 wt %.

Aspect 73. The method of any one of Aspect 1-Aspect 72, wherein the catalyst promoter is present in an amount from about 0.5 wt % to about 12 wt %.

Aspect 74. The method of claim Aspect 57, wherein the catalyst promoter is present in an amount from about 0.5 wt % to about 10 wt %.

Aspect 75. The method of claim Aspect 57, wherein the catalyst promoter is present in an amount from about 0.5 wt % to about 8 wt %.

Aspect 76. The method of claim Aspect 57, wherein the catalyst promoter is present in an amount from about 0.5 wt % to about 6 wt %.

Aspect 77. The method of claim Aspect 57, wherein the catalyst promoter is present in an amount from about 0.5 wt % to about 4 wt %.

Aspect 78. The method of claim Aspect 57, wherein the catalyst promoter is present in an amount from about 0.5 wt % to about 2 wt %.

Aspect 79. The method of claim Aspect 57, wherein the catalyst promoter is present in an amount from about 1 wt % to about 12 wt %.

Aspect 80. The method of claim Aspect 57, wherein the catalyst promoter is present in an amount from about 1 wt % to about 10 wt %.

Aspect 81. The method of claim Aspect 57, wherein the catalyst promoter is present in an amount from about 1 wt % to about 8 wt %.

Aspect 82. The method of claim Aspect 57, wherein the catalyst promoter is present in an amount from about 1 wt % to about 6 wt %.

Aspect 83. The method of claim Aspect 57, wherein the catalyst promoter is present in an amount from about 1 wt % to about 4 wt %.

Aspect 84. The method of claim Aspect 57, wherein the catalyst promoter is present in an amount from about 1 wt % to about 2 wt %.

Aspect 85. The method of any one of Aspect 1-Aspect 84, wherein the catalyst promoter is K, Cs, or combination thereof.

Aspect 86. The method of claim Aspect 85, wherein the catalyst promoter is K.

Aspect 87. The method of claim Aspect 85, wherein the catalyst promoter is Cs.

Aspect 88. The method of any one of Aspect 1-Aspect 87, wherein the catalyst promoter is present in an amount from about 0.1 wt % to about 7 wt %.

Aspect 89. The method of claim Aspect 88, wherein the catalyst promoter is present in an amount from about 1.5 wt % to about 6.5 wt %.

Aspect 90. The method of claim Aspect 88, wherein the catalyst promoter is present in an amount from about 2 wt % to about 6 wt %.

Aspect 91. The method of any one of Aspect 1-Aspect 90, wherein the catalyst metal is present in an amount from about 1 wt % to about 8 wt %.

Aspect 92. The method of claim Aspect 91, wherein the catalyst promoter is present in an amount from about 2 wt % to about 6 wt %.

Aspect 93. The method of claim Aspect 91, wherein the catalyst promoter is present in an amount from about 3 wt % to about 5 wt %.

Aspect 94. The method of claim Aspect 91, wherein the catalyst promoter is present in an amount from about 3.9 wt % to about 4.9 wt %.

Aspect 95. The method of any one of Aspect 1-Aspect 94, wherein the total wt % of both the catalyst metal and the catalyst promoter is from about 1 wt % to about 15 wt %.

Aspect 96. The method of claim Aspect 95, wherein the total wt % of both the catalyst metal and the catalyst promoter is from about 1 wt % to about 10 wt %.

Aspect 97. The method of claim Aspect 95, wherein the total wt % of both the catalyst metal and the catalyst promoter is from about 2 wt % to about 10 wt %.

Aspect 98. The method of claim Aspect 95, wherein the total wt % of both the catalyst metal and the catalyst promoter is from about 3 wt % to about 10 wt %.

Aspect 99. The method of claim Aspect 95, wherein the total wt % of both the catalyst metal and the catalyst promoter is from about 4 wt % to about 10 wt %.

Aspect 100. The method of claim Aspect 95, wherein the total wt % of both the catalyst metal and the catalyst promoter is from about 5 wt % to about 10 wt %.

Aspect 101. The method of any one of Aspect 1-Aspect 100, wherein the heterogeneous catalyst has a particle size from about 10 nm to about 50 μm.

Aspect 102. The method of any one of Aspect 1-Aspect 101, wherein catalyst support comprises $CeO_2$.

Aspect 103. The method of any one of Aspect 1-Aspect 101, wherein catalyst support comprises $La_2O_3$.

Aspect 104. The method of any one of Aspect 1-Aspect 101, wherein catalyst support comprises $CeO_2$ and $La_2O_3$; and wherein the $CeO_2$ and $La_2O_3$ are present in a 1:1 ratio based on weight.

Aspect 105. The method of any one of Aspect 1-Aspect 104, wherein catalyst support has a particle size from about 10 nm to about 50 μm.

Aspect 106. The method of any one of Aspect 1-Aspect 105, wherein the catalyst support is $CeO_2$.

Aspect 107. The method of any one of Aspect 1-Aspect 105, wherein the catalyst support is $La_2O_3$.

Aspect 108. The method of any one of Aspect 1-Aspect 107, wherein the catalyst the catalyst metal has a particle size of from about 0.1 nm to about 1 μm.

Aspect 109. The method of claim Aspect 108, wherein the catalyst the catalyst metal has a particle size of from about 1 nm to about 100 nm.

Aspect 110. The method of claim Aspect 108, wherein the catalyst the catalyst metal has a particle size of from about 1 nm to about 50 nm.

Aspect 111. The method of claim Aspect 108, wherein the catalyst the catalyst metal has a particle size of from about 1 nm to about 20 nm.

Aspect 112. The method of claim Aspect 108, wherein the catalyst the catalyst metal has a particle size of from about 1 nm to about 15 nm.

Aspect 113. The method of claim Aspect 108, wherein the catalyst the catalyst metal has a particle size of from about 1 nm to about 10 nm.

Aspect 114. The method of any one of Aspect 1-Aspect 113, wherein the catalyst comprises a zeolite, a solid acid catalyst, or a combination thereof.

Aspect 115. The method of Aspect 114, wherein the zeolite comprises ZSM-5, a Y-zeolite, USY zeolite, zeolite X, or a combination thereof.

Aspect 116. The method of Aspect 115 wherein the zeolite comprises ZSM-5.

Aspect 117. The method of Aspect 114, wherein the solid acid comprises $ZrO_2/SO_4$, $TiO_2/SO_4$, $HfO_2/SO_4$, $ZrO_2/WO_3$, $TiO_2/WO_3$, $HfO_2/WO_3$, or a combination thereof.

Aspect 118. The method of any of Aspect 1-Aspect 117, wherein the catalyst comprises a metal promoter.

Aspect 119. The method of Aspect 118, wherein the metal promoter comprises Pt, Pd, Ru, Rh, Co, Mb, Ni, Fe, Mn, or a combination thereof.

Aspect 120. The method of Aspect 119, wherein the catalyst comprises $Pt/ZrO_2/SO_4$.

Aspect 121. The method of any of Aspect 1-Aspect 120, wherein the catalyst and waste plastic are present in a ratio from about 20:1 to about 1:20.

Aspect 122. The method of claim Aspect 121, wherein the catalyst and waste plastic are present in a ratio from about 10:1 to about 1:1.

Aspect 123. The method of claim Aspect 121, wherein the catalyst and waste plastic are present in a ratio of about 10:1.

Aspect 124. The method of any of Aspect 1-Aspect 123, wherein microwave irradiation is applied to the reaction mixture for from about 5 minutes to about 30 minutes.

Aspect 125. The method of any of Aspect 1-Aspect 124, wherein the microwave irradiation has a frequency of from about 915 MHz to about 20 GHz.

Aspect 126. The method of any of Aspect 1-Aspect 124, wherein the microwave irradiation has a frequency of from about 915 MHz to about 10 GHz.

Aspect 127. The method of any of Aspect 1-Aspect 124, wherein the microwave irradiation has a frequency of from about 915 MHz to about 6.65 GHz.

Aspect 128. The method of any of Aspect 1-Aspect 127, wherein the microwave irradiation induces bulk temperatures in the reaction mixture of from about 180° C. to about 400° C.

Aspect 129. The method of Aspect 128, wherein the microwave irradiation induces a bulk temperature in the reaction mixture of about 250° C. to 360° C.

Aspect 130. The method of Aspect 128, wherein the microwave irradiation induces bulk temperatures in the reaction mixture of from about 260° C. to about 350° C.

Aspect 131. The method of any of Aspect 1-Aspect 129, wherein the microwave irradiation is applied to the reaction mixture in an inert atmosphere.

Aspect 132. The method of Aspect 131, wherein the inert atmosphere comprises nitrogen.

Aspect 133. The method of any of Aspect 1-Aspect 132, wherein the value-added product comprises from about 10 vol % to about 70 vol % hydrogen.

Aspect 134. The method of Aspect 133, wherein the value-added product comprises from about 35 vol % to about 70% hydrogen.

Aspect 135. The method of any of Aspect 1-Aspect 134, wherein the value-added product comprises a mixture of toluene and benzene; and wherein the product comprises from about 5 vol % to about 40 vol % of the mixture of toluene and benzene.

Aspect 136. The method of any of Aspect 1-Aspect 135, wherein the value-added product comprises from about 1 vol % to about 15 vol % toluene.

Aspect 137. The method of any of Aspect 1-Aspect 136, wherein the value-added product comprises from about 5 vol % to about 40 vol % benzene.

Aspect 138. The method of any of Aspect 1-Aspect 137, wherein the value-added product comprises from about 5 vol % to about 75 vol % ethylene.

Aspect 139. The method of any of Aspect 1-Aspect 138, wherein the value-added product comprises from about 5 vol % to about 25 vol % methane.

Aspect 140. The method of any of Aspect 1-Aspect 139, wherein the method is carried out in a fixed-bed reactor.

Aspect 141. The method of any of Aspect 1-Aspect 139, wherein the method is carried out in a moving bed reactor.

Aspect 142. The method of any of Aspect 1-Aspect 141, wherein the method is carried out at a pressure of from about 1 to about 20 atm.

Aspect 143. The method of Aspect 142, wherein the method is carried out at pressure of from about 1 to about 10 atm.

Aspect 144. The method of Aspect 142, wherein the method is carried out at pressure of from about 5 atm.

Aspect 145. The method of Aspect 142, wherein the method is carried out at pressure of from about 1 atm.

Aspect 146. A composition comprising at least one value-added product produced by the method of any of Aspect 1-Aspect 145.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Materials

Low-density polyethylene (LDPE) was used as a typical waste plastic feed for some microwave-assisted catalytic conversion experiments. Other waste plastics including high-density polyethylene (HDPE), polypropylene (PP), polystyrene (PS), polyethylene terephthalate (PET), polyurethanes (PU), clothing fibers, and epoxy plastics were also converted under microwave irradiation as disclosed herein.

ZSM-5 (Zeolyst International, Catalog Number CBV 2314) was used for some experiments. This catalyst has an $SiO_2/Al_2O_3$ mole ratio of 23:1, a nominal cation form of ammonium, a 0.05 $Na_2O$ wt %, and a surface area of 425 $m^2/g$.

Example 2

Methods

A variable frequency microwave reactor (Lambda MC1330-200) was used for the microwave-assisted catalysis, with the frequency set at 5850 MHz in most experiments, but not limited by a fixed frequency for these reactions in general. The bulk sample temperature was measured in the microwave reaction using infrared (IR) thermography via an IR sensor.

The catalyst (ZSM-5) and waste plastic (LDPE) were ground up to about micron-sized particles and mixed with a respective 10:1 mass ratio, although other mass ratios will also work. The mixture mass was about 0.5 g and about 0.6 $cm^3$ in volume. The mixture was held within loose quartz wool packing in the quartz tube for the decomposition (see FIG. 1).

A 20 mL/min flow rate of dinitrogen ($N_2$) introduced at room temperature was used as a carrier gas and as an internal standard for calculation, the flow rate doesn't need fixed. The sample heat up at 260° C. and 360° C. for reaction. 260° C. is the lowest temperature that can be reached due to microwave reactor parameters; however, lower reaction temperatures (e.g. 180° C.) are expected to work for the disclosed conversion process. Traditional thermal decomposition was also performed as a control using an 800 W furnace with a surface thermocouple used to measure sample temperature. A quartz tube (8 mm ID, 12 mm OD) was used as a fixed bed reactor for both heating methods. The output gas composition was measured by an on-line 4-channel Inficon Fusion micro gas chromatograph (Micro-GC).

Example 3

Plastic Waste Decomposition Using a Microwave Reactor

Figure 2C:
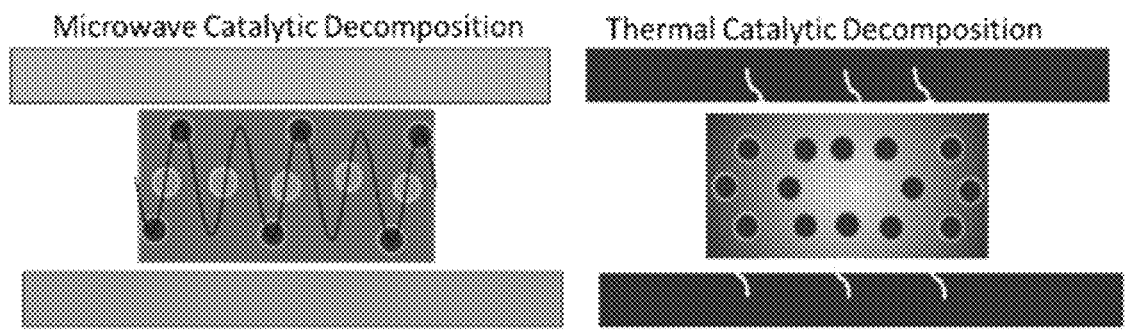
Figure 2C:
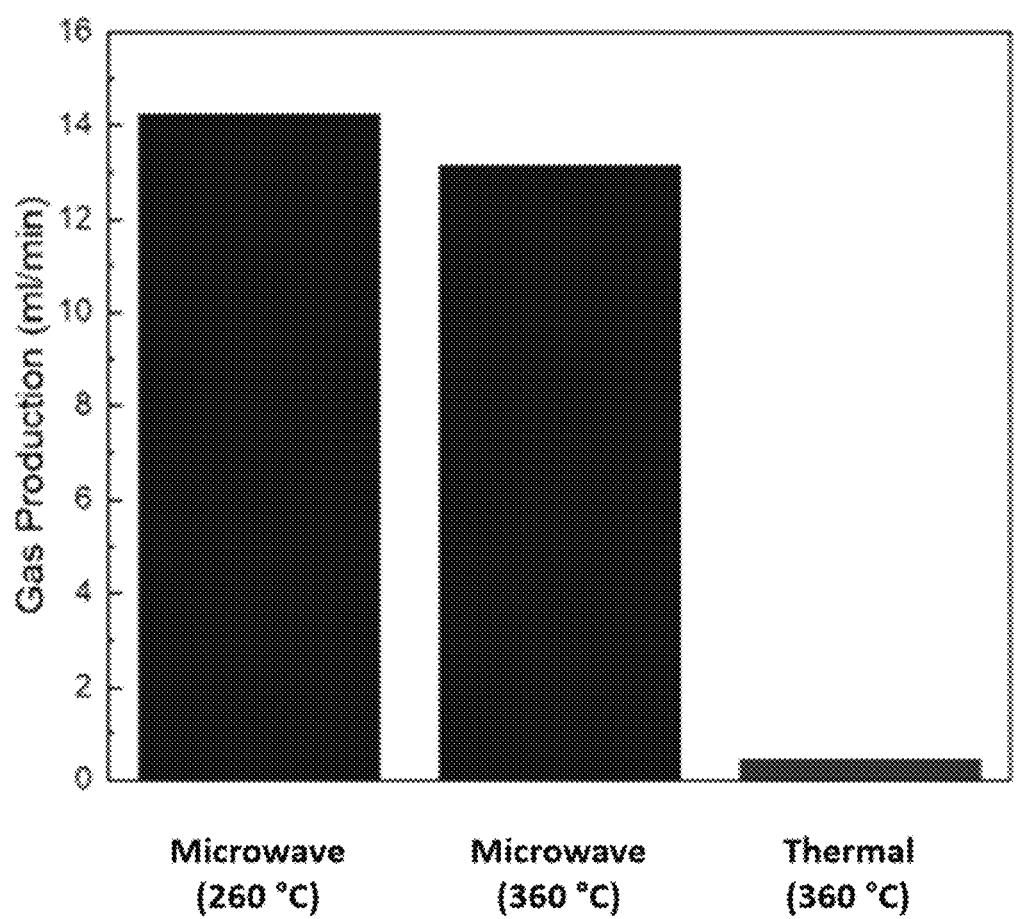

After 9 min of contact using traditional thermal (800 W furnace) heating at 360° C., there was almost no LDPE decomposition, as much less gas (<1 mL/min) was produced and no liquid detected (see FIG. 2). In microwave reaction conditions, when the bulk sample temperature reached 360° C., the LDPE decomposed and gas production reached 13 mL/min along with production of a trace amount of liquid. The LDPE also decomposed with 14 mL/min of gas production at an even lower microwave reaction temperature of 260° C.

Figure 3A:
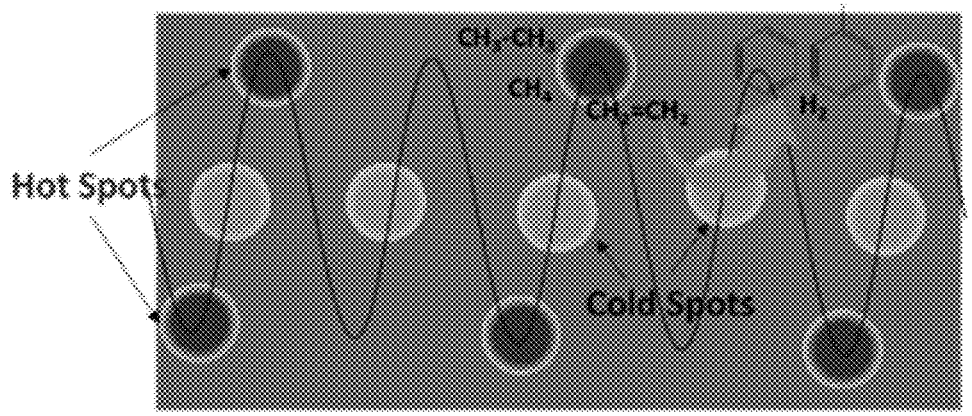
FIGS. 3A-3B show a schematic of microwave-assisted catalytic decomposition of plastic waste and representative data showing selectivity of hydrocarbon and hydrogen products using a disclosed microwave-assisted catalytic decomposition method.
Figure 3B:
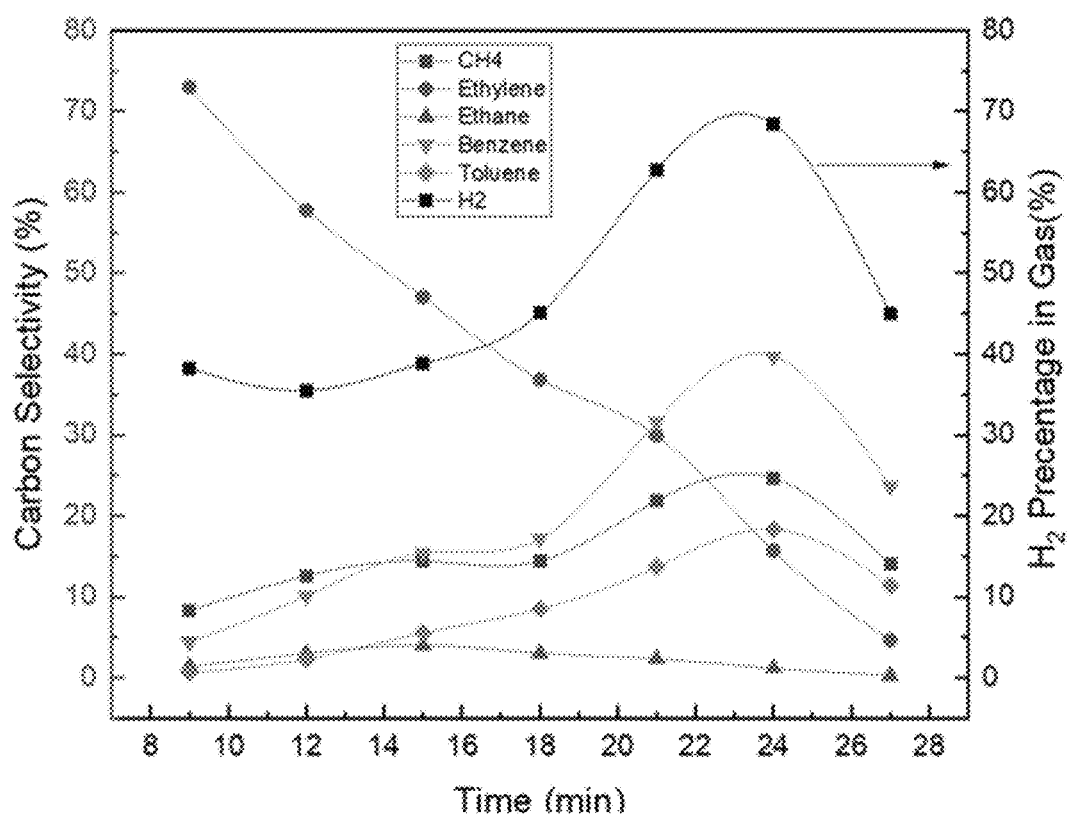

Reaction progress was measured by an inline GC; the gas composition changed in 360° C. (FIG. 3B). In the early stages of the microwave reaction, the gas is mainly composed of $H_2$ and light olefins, especially ethylene (up to 75% in hydrocarbon gas). By comparison, ethylene mainly formed at over 800° C. using traditional thermal decomposition. As the reaction proceeded, the ethylene selectivity in hydrocarbons dropped quickly, while the selectivity for benzene and toluene rapidly increased up to 58% in total after 24 min. This is likely because the ethylene reacted to form aromatics, (e.g. $3C_2H_4 \rightarrow C_6H_6+3H_2$), with a rapid increase of $H_2$ percentage as confirmation.

We have thus shown that plastic waste decomposes to produce aromatics at low (<360° C.) temperatures. With conventional thermal decomposition technology, aromatics can be produced at relatively higher temperature (650 to 800° C.) with lower yields (20%); otherwise lighter olefins are produced at over 800° C. and aromatization occurs in a second step. The aromatic formation activity with microwave catalysis is high because of the unique mode by which microwave heating occurs: the catalyst absorbs microwave energy and subsequently transfers heat to the plastic waste via conduction. This makes some catalysts have much higher temperatures than the plastic particles, especially those catalyst particles located at microwave peaks and troughs (i.e., "hot spots"). Other catalyst particles will be colder than those located at hot spots, especially those located at "cold spots" (i.e., at the zero line of the microwave form) Over the hot spots, plastic will catalytically gasify to form light olefins, whereas over the cold spots, the light olefins will aromatize and produce $H_2$ (FIG. 3A).

Figure 4:
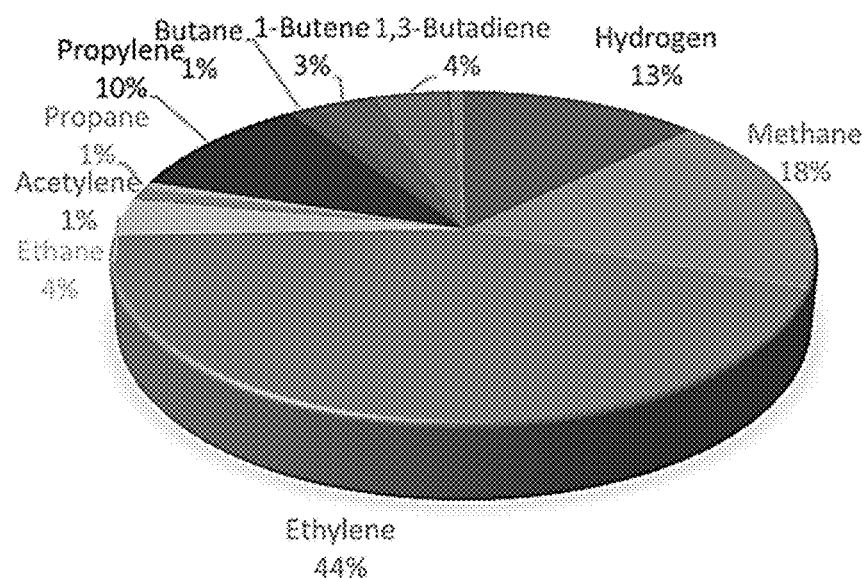
FIG. 4 shows representative data for the relative amounts of product materials produced using a disclosed microwave-assisted catalytic decomposition method with polyethylene as a reactant material. The data show that the method provides for conversion of polyethylene to C2-C4 olefins and hydrogen using a SiC catalyst.

Additional examples of plastic waste decomposition are provided in FIGS. 4-7. FIG. 4 shows representative data for the relative amounts of product materials produced using a disclosed microwave-assisted catalytic decomposition method with polyethylene as a reactant material. The data show that the method provides for conversion of polyethylene to C2-C4 olefins and hydrogen using a SiC catalyst.

Figure 5:
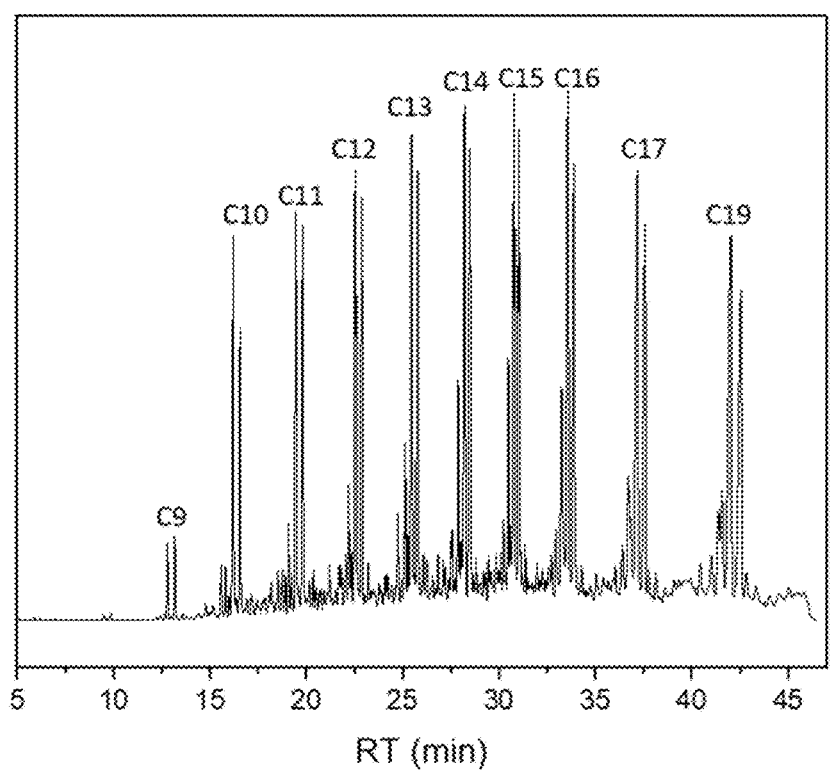
FIG. 5 shows determination of products by GC-MS using a SiC catalyst with low density polyethylene waste plastic. Heating was carried out with a temperature ramping program set at 20° C. per min until a bulk temperature of 300° C. was reached and then maintained at this temperature for 1 h. The data show production of alkanes and olefins. In the figure, the C number labels in the GC-MS trace indicate number of carbons in the hydrocarbon product detected. For the data shown, the reaction was carried out using 1 g of polyethylene and 2 g of SiC catalyst.

FIG. 5 shows determination of products by GC-MS using a SiC catalyst with low density polyethylene waste plastic. Heating was carried out with a temperature ramping program set at 20° C. per min until a bulk temperature of 300° C. was reached and then maintained at this temperature for 1 h. The data show production of alkanes and olefins. In the figure, the C number labels in the GC-MS trace indicate number of carbons in the hydrocarbon product detected. For the data shown, the reaction was carried out using 1 g of polyethylene and 2 g of SiC catalyst.

Figure 6:
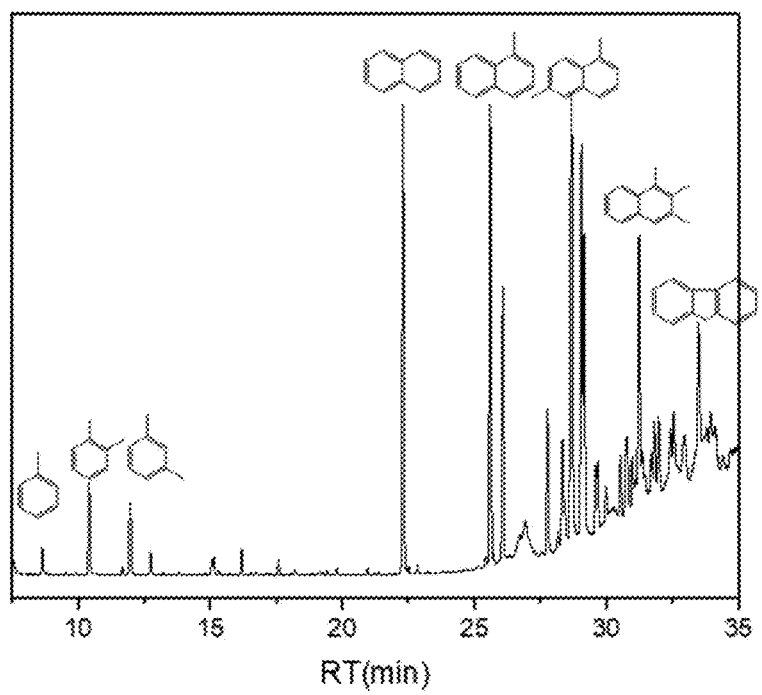
FIG. 6 shows determination of products by GC-MS using ZSM-5 with low density polyethylene waste plastic having $M_w$ ~4,000 by GPC and average $M_n$ ~1,700 by GPC. Heating was carried out with a temperature ramping program set at 20° C. per min until a bulk temperature of 300° C. was reached and then maintained at this temperature for 1 h. The data show production of alkanes, olefins, and aromatics. For the data shown, the reaction was carried out using 1 g of polyethylene and 1 g of ZSM-5 catalyst.

FIG. 6 shows determination of products by GC-MS using ZSM-5 with low density polyethylene waste plastic having $M_w$ ~4,000 by GPC and average $M_n$ ~1,700 by GPC. Heating was carried out with a temperature ramping program set at 20° C. per min until a bulk temperature of 300° C. was reached and then maintained at this temperature for 1 h. The data show production of alkanes, olefins, and aromatics. For the data shown, the reaction was carried out using 1 g of polyethylene and 1 g of ZSM-5 catalyst.

Figure 7:
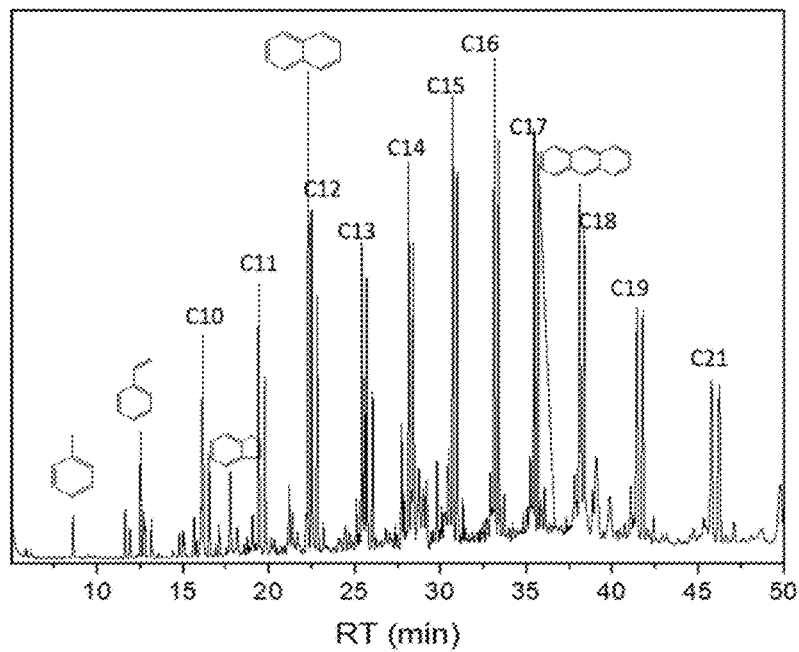
FIG. 7 shows determination of products by GC-MS using metal oxide catalyst with with low density polyethylene waste plastic having $M_w$ ~4,000 by GPC and average $M_n$ ~1,700 by GPC. Heating was carried out with temperature ramping program set at 20° C. per min until a bulk temperature of 300° C. was reached and then maintained at this temperature for 1 h. The data show production of a mixture of alkanes, olefins, and aromatic products. For the data shown, the reaction was carried out using 1 g of polyethylene and 3 g of metal oxide catalyst. The metal oxide catalyst was CsRu/CeO$_2$ comprising 2 wt % Cs and 4 wt % Ru.

FIG. 7 shows determination of products by GC-MS using metal oxide catalyst with with low density polyethylene waste plastic having $M_w$ ~4,000 by GPC and average $M_n$ ~1,700 by GPC. Heating was carried out with temperature ramping program set at 20° C. per min until a bulk temperature of 300° C. was reached and then maintained at this temperature for 1 h. The data show production of a mixture of alkanes, olefins, and aromatic products. For the data shown, the reaction was carried out using 1 g of polyethylene and 3 g of metal oxide catalyst. The metal oxide catalyst was CsRu/CeO$_2$ comprising 2 wt % Cs and 4 wt % Ru.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for converting a waste plastic to a value-added product, the method comprising:
   (a) providing a waste plastic to a reactor;
   (b) contacting the waste plastic with a catalyst to form a reaction mixture; and
   (c) applying microwave radiation to the reaction mixture; thereby forming a value-added product;
   wherein the catalyst comprises rare-earth metal oxide catalyst;
   wherein the rare-earth metal oxide catalyst comprises a catalyst metal comprising at least one metal selected from Groups 6-12 and a catalyst support selected from CeO$_2$, La$_2$O$_3$, and combinations thereof;
   wherein the microwave irradiation induces bulk temperatures in the reaction mixture of from about 180° C. to about 400° C.;
   wherein the value-added product comprises hydrogen and at least one hydrocarbon selected from benzene, toluene, xylenes, ethylene, propylene, butene, and methane; and
   wherein the value-added product comprises from about 10 mol % to about 70 mol % hydrogen.

2. The method of claim 1, wherein the waste plastic comprises a material selected from a polyamide, a polycarbonate, a polyvinyl chloride, a polyester, a polyolefin, an epoxy, and combinations thereof.

3. The method of claim 1, wherein the waste plastic comprises a polyolefin.

4. The method of claim 3, wherein the polyolefin is selected from a polyolefin low-density polyethylene, a high-density polyethylene, a polypropylene, a polystyrene, and combinations thereof.

5. The method of claim 1, wherein the catalyst metal is selected from Ru, Pt, Pd, Cr, Mn, Fe, Co, Ni, Zn, and combinations thereof.

6. The method of claim 1, wherein the catalyst metal is present in an amount from about 0.1 wt % to about 15 wt %; and wherein the wt % is based on the total weight of the catalyst support and the catalyst metal.

7. The method of claim 1, wherein the rare-earth metal oxide catalyst further comprises a catalyst promoter; and wherein the catalyst promoter comprises at least one metal selected from Group 1, and Group 2.

8. The method of claim 7, wherein the catalyst promoter is selected from K, Cs, and a combination thereof.

9. The method of claim 7, wherein the catalyst promoter is present in an amount from about 0.1 wt % to about 15 wt %; and wherein the wt % is based on the total weight of the catalyst support, the catalyst metal, and the catalyst promoter.

10. The method of claim 1, wherein the microwave irradiation has a frequency of from about 915 MHz to about 20 GHz.

11. The method of claim 1, wherein the method is carried out at a pressure of from about 1 to about 20 atm.

12. The method of claim 1, wherein the microwave irradiation induces bulk temperatures in the reaction mixture of from about 260° C. to about 350° C.

13. The method of claim 1, wherein the value-added product comprises a mixture of toluene and benzene; and wherein the product comprises from about 5 mol % to about 40 mol % of the mixture of toluene and benzene.

14. The method of claim 1, wherein the reactor is a fixed-bed reactor or a moving bed reactor.

* * * * *